(12) United States Patent
Chen

(10) Patent No.: US 11,707,091 B2
(45) Date of Patent: *Jul. 25, 2023

(54) ATOMIZING NOZZLE AND ELECTRONIC ATOMIZING INHALER

(71) Applicant: Shenzhen Smoore Technology Limited, Shenzhen (CN)

(72) Inventor: Zhiping Chen, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 388 days.

This patent is subject to a terminal disclaimer.

(21) Appl. No.: 16/994,726

(22) Filed: Aug. 17, 2020

(65) Prior Publication Data

US 2020/0375248 A1    Dec. 3, 2020

Related U.S. Application Data

(63) Continuation of application No. 15/966,616, filed on Apr. 30, 2018, now Pat. No. 10,791,764, which is a (Continued)

(30) Foreign Application Priority Data

May 12, 2011   (CN) .......................... 201110125093.7

(51) Int. Cl.
*A24F 40/44*    (2020.01)
*A24F 40/42*    (2020.01)
(Continued)

(52) U.S. Cl.
CPC .............. *A24F 40/44* (2020.01); *A24F 40/42* (2020.01); *A24F 40/46* (2020.01); *A24F 40/48* (2020.01);
(Continued)

(58) Field of Classification Search
CPC ....... A61M 11/042; A24F 40/10; A24F 40/40; A24F 40/42; A24F 40/44; A24F 40/46; A24F 40/48; A24F 40/485
See application file for complete search history.

(56) References Cited

U.S. PATENT DOCUMENTS 7,832,410 B2   11/2010   Hon
9,504,279 B2   11/2016   Chen
(Continued)

FOREIGN PATENT DOCUMENTS

CN    101228969 A    7/2000
CN    2719043 Y      8/2005
(Continued)

OTHER PUBLICATIONS

Machine translation of WO-2010140841 from WIPO.*
(Continued)

*Primary Examiner* — Joseph D. Boecker
(74) *Attorney, Agent, or Firm* — Mark R. Malek; Widerman Malek, PL

(57) ABSTRACT

An atomizer of an electronic atomizing inhaler, includes a casing body, provided with a cap at the opening of the front end, with a gas-outlet aperture on the cap, and provided with a rear closure at the opening of the rear end, with a gas-inlet aperture on the rear closure; a liquid-container and a heater (Continued)

provided in the cavity formed by the casing body, the cap and the rear closure, an airflow-passage being provided between the casing body and the liquid-container; a liquid-guiding device closing the mouth part of the liquid-container, with no liquid-storage medium provided in the liquid-container; and a heater provided on the top of the rear closure, contacting the lower surface of the liquid-guiding device. An electronic atomizing inhaler is also provided.

18 Claims, 4 Drawing Sheets

Related U.S. Application Data continuation of application No. 14/582,239, filed on Dec. 24, 2014, now Pat. No. 9,980,513, which is a continuation of application No. 13/824,335, filed as application No. PCT/CN2012/000347 on Mar. 19, 2012, now Pat. No. 9,504,279.

(51) Int. Cl.

| | | |
|---|---|---|
| *A24F 40/485* | (2020.01) | |
| *A24F 40/48* | (2020.01) | |
| *A24F 40/46* | (2020.01) | |
| *A61M 11/04* | (2006.01) | |
| *H05B 3/80* | (2006.01) | |
| *A24F 40/10* | (2020.01) | |
| *A61M 11/00* | (2006.01) | |

(52) U.S. Cl.
CPC ........... *A24F 40/485* (2020.01); *A61M 11/00* (2013.01); *A61M 11/042* (2014.02); *H05B 3/80* (2013.01); *A24F 40/10* (2020.01)

(56) References Cited

U.S. PATENT DOCUMENTS 9,980,513 B2 * 5/2018 Chen ..................... A61M 11/00
10,791,764 B2 * 10/2020 Chen ..................... A24F 40/44

FOREIGN PATENT DOCUMENTS

| | | |
|---|---|---|
| CN | 2889333 Y | 4/2007 |
| CN | 201104488 Y | 8/2008 |
| CN | 201379071 Y | 1/2010 |
| CN | 101843368 A | 9/2010 |
| CN | 101862038 A | 10/2010 |
| CN | 102326869 A | 1/2012 |
| WO | 2009155734 A1 | 12/2009 |
| WO | WO-2010140841 A2 * | 12/2010 ............ A61M 15/06 |

OTHER PUBLICATIONS

The State Intellectual Property Office of People's Republic of China, The First Office Action, Application No. 201110125093.7 dated Aug. 31, 2012.
International Search Report in related application PCT/CN2012/000347 dated Jul. 5, 2012; 2 pages.
Written Opinion in related application PCT/CN2012/000347 dated Jul. 5, 2012; 6 pages.

* cited by examiner

— ATOMIZING NOZZLE AND ELECTRONIC ATOMIZING INHALER —

REFERENCE TO RELATED APPLICATIONS

This application is a continuation of U.S. application Ser. No. 15/966,616, filed on Apr. 30, 2018, which is a continuation of U.S. application Ser. No. 14/582,239, filed on Dec. 24, 2014, which is a continuation of U.S. application Ser. No. 13/824,335, filed on Sep. 21, 2013, now U.S. Pub. No. 2014/0007863, published Jan. 9, 2014, which is a national stage application under 35 U.S.C. 371 of PCT Application No. PCT/CN2012/000347 having an international filing date of Mar. 19, 2012, which designated the United States, which PCT application claimed the benefit of China Application No. 201110125093.7 filed May 12, 2011, the entire disclosure of each of which are incorporated herein by reference.

FIELD OF THE INVENTION

The present invention relates to an electronic atomizing apparatus which is used for atomizing an aromatic liquid for a user to inhale, and especially relates to an atomizer and an electronic atomizing inhaler having the atomizer.

BACKGROUND OF THE INVENTION

Electronic atomizers which yielding tobacco components or other materials in an inhalable form are normally used to substitute traditional smoking articles based upon combusting tobacco, or used as an inhalator for the inhalation of medicaments for treating respiratory diseases. A typical atomizer comprises a cylindrical part containing a power supply and a control system, a liquid-atomizing part connected to the cylindrical part, and a suction nozzle. According to the prior art, the liquid-atomizing part and the suction nozzle can be incorporated to be as a single piece, alternatively, the liquid atomizing part and the suction nozzle also can be arranged separately and are connected to each other by inserting or bonding.

A typical structure of the prior art is disclosed in Chinese patent ZL200420031182.0 entitled "Atomizing electronic cigarette", including a casing body 14 and a suction nozzle 15. An inlet port 4 provided on the outer wall of the casing body 14, an electronic circuit board 3, an ordinary pressure chamber 5, a sensor 6, a gas-liquid separator 7, an atomizer 9 and a liquid-supplying bottle 11 are successively mounted in the casing body 14. A multi-apertured part 28 for containing liquid is provided in the liquid-supplying bottle 11. The atomizer 9 is held in contact with the supplying bottle 11 by a formation 36. An atomizing chamber 10 is provided in the atomizer 9. A shielding ring 13 for enclosing the liquid-supplying bottle 11 is provided between one side of the liquid-supplying bottle 11 and the casing body 14. A gas passage 12 is provided on another side of the liquid-supplying bottle 11. The inlet port 4, the ordinary pressure chamber 5, the gas-liquid separator 7, the atomizer 9, the gas passage 12, the air-draining port 17 and the suction nozzle 15 are communicated with each other and arranged successively. The structure provided by the previous mentioned patent, which utilizing capillarity action of the liquid for the atomizer 9, adopting a ceramic for the atomizing chamber 10, inhaling the liquid from the liquid-supplying bottle 11 using foamed metal, so as to atomize the liquid in the atomizing chamber 10 at high temperature, and arranging the gas-liquid separator 7 on the gas passage 12, dramatically improves the traditional electronic cigarette products which utilizes ultrasound and mechanical atomizing technology. Whilst the structure described above has a complicated structure and a high manufacturing cost, and it is difficult to assemble the above mentioned parts of the structure. Additionally, the multi-apertured part 28 provided in the liquid-supplying bottle 11 also leads to the decrease of the liquid volume contained in the liquid-supplying bottle 11.

Another typical structure of the prior art is disclosed in Chinese patent ZL200720057873.1 entitled "Non-ignitable atomizing electronic cigarette", including a controller and a generator, wherein a cover with an indicator lamp, a power supply, an integral circuit board, a mini gas-transmission switch and a connecting conductor are successively provided in the controller, and wherein a connecting conductor, a secondary pressure-maintaining chamber, a liquid-resisting flat, a secondary liquid-storage chamber, a heating apparatus, a liquid-draining mechanism, a liquid-storage chamber and a suction nozzle are successively provided in the generator. A gas-inlet port is provided on one side of the connecting conductor of the generator, and a through-aperture is provided between the controller and the connecting conductor of the generator. Although there is an improvement bases on the prior art, whilst just like the technical proposal disclosed in ZL200420031182.0, the heating apparatus is provided in the liquid-draining mechanism, resulting in the limitation of the material for forming the liquid-draining mechanism which needs to be hard, and the tendency of collapse of the liquid-draining mechanism during assembling. Further, the liquid is also difficult to be transmitted from the liquid-draining mechanism to the secondary liquid-storage chamber. In addition, the liquid volume possibility to be stored in the storage chamber is insufficient because of the storage chamber being made of medicinal cotton fibre.

Another kind of typical structure of the prior art is disclosed in Chinese patent ZL200820124683.1 entitled "Disposable Integrated Electronic Atomizing Inhalator", including a rod body, and a plurality of parts successively contained in the rod body from bottom to top which comprising: a terminal connected to the interior wall of the rod body, which is used for connecting an electronic smoking pipe; a terminal core provided on the terminal in electrical connection with the electrode of the electronic smoking pipe; an atomizer electrically connected with the terminal core, which is used for atomizing by heating when it is electrified, the atomizer having a gas-vent aperture provided therein; an insert part provided on the atomizer, with liquid-storage medium inside for absorbing or storing the tobacco liquid to be atomized; a top cover inserted into the top end of the rod body for sealing and preventing the back-flow of the tobacco liquid, the top cover having a gas-passing aperture defined thereon.

Neither the path for the tobacco liquid being transmitted to the gas-passing aperture nor the process of how the heating apparatus atomizes the tobacco liquid is disclosed in the description of the electronic atomizing inhalator mentioned above. In addition, according to the drawings of the above mentioned electronic atomizing inhalator, one end of the insert part of the electronic atomizing inhalator is totally exposed. The volume of the tobacco liquid in the insert part is totally depending on the absorbing of the liquid-storage medium, while the volume of the tobacco liquid being absorbed by the liquid-storage medium is insufficient. On the other hand, once the volume absorbed by the medium excesses a little, it is easy to form a liquid-drop and then the liquid-drop will drop on the frame of the atomizer and deposit on the bottom of the atomizer. The tobacco liquid will be charred eventually when the atomizer having heat-storage function and soaking function. In addition, it is difficult for the tobacco liquid deposited on the bottom of the atomizer to be drained out from the gas passage.

SUMMARY OF THE INVENTION

Under the current situation of the relatively developed and stable electronic controlling technology, it is especially important to develop the structure of the atomizer for the electronic atomizing product, in order to obtain a better electronic atomizing product which has a simple structure, and is easy to assemble and convenient and safe to use. One of the main problems trying to be resolved by the present invention is to increase the volume of the liquid being atomized as much as possible, in order to allow people to inhale easily and also to make it easy to assemble and store and safe to use with simple structure.

Thereof, based on the prior-art, in one aspect of the present invention, an atomizer of an electronic atomizing inhaler is provided comprising: a tubular casing body with a cavity formed therein and two openings at front and rear ends thereof communicated with the cavity, the cavity and the openings communicating with each other to form an airflow-passage; a cap provided at the opening of the front end of the casing body, a gas-outlet aperture being defined in the cap and communicated with the airflow-passage; a rear closure provided at the opening of the rear end of the casing body, a gas-inlet aperture being defined in the rear closure and communicated with the airflow-passage; a liquid-container provided in the cavity of the casing body with liquid contained therein and no liquid-storage medium contained therein, the liquid-container having a mouth part facing towards the rear closure; a liquid-guiding device positioned between the mouth part of the liquid-container and the rear closure, the liquid-guiding device closing the mouth part of the liquid-container and a connection-passage for connecting the airflow-passage and the gas-inlet aperture being formed between the liquid-guiding device and the rear closure; and a heater provided on the top of the rear closure and connecting the liquid-guiding device, at least part of the heater being located in the connection-passage.

In another aspect of the present invention, an electronic atomizing inhaler having the atomizer is also provided.

The electronic atomizing inhaler is a kind of product used to atomize the liquid contained inside for a consumer to inhale the atomized gas, which at least comprises an atomizer part and a controlling power part connected to each other by a screw electrode; in which, the controlling power part applies the electric power for the heater in the atomizer; the heater being used to atomize the liquid in the atomizer for the consumer to inhale. The liquid-container and heater are provided in the atomizer. The atomizer can be manufactured and assembled as independent parts because the liquid-container, the liquid-guiding device and the heater are provided in the cavity which is formed by the casing body, the cap and the rear closure. The atomizer can be used as a disposable part in use, which is to say that when there is no liquid left in the atomizer, the atomizer can be replaced conveniently and safely. The consumer inhales the atomized gas in the atomizer from the cap.

The cap provided at the opening of the front end of the casing body can be either just a wall plugging the opening of the front end of the casing body, or a cap-shaped cover covering and closing the opening of the front end of the casing body by way of insertion, screwing or bonding. The gas-outlet aperture provided on the cap is used for the convenient outflow of the atomized gas, so that the consumer can inhale the atomized gas in the atomizer via the gas-outlet aperture.

The rear closure at first should be a part which can plug the opening of the rear end of the casing body, so as to form the cavity together with the casing body and the cap; then, the rear closure is also used for supporting the heater against the lower surface of the liquid-guiding device. The liquid-guiding device is supported by the upper end of the rear closure to prevent the liquid-guiding device falling from the mouth part of the liquid-container. A sealing ring can be provided between the back end of the rear closure and the inside wall of the casing body, so as to prevent the liquid dropping on the rear closure flowing out of the casing body, in addition, it is very convenient to assemble the rear closure and the casing body by insertion when the sealing ring has been provided, especially when there is a problem of thermal expansion and contraction of the casing body, the sealing ring can automatically adapt to the different space between the rear closure and the casing body, so as to achieve a good sealing effect.

For the convenience of manufacture, the rear closure can be separated into two parts, namely a fixing seat and a sealing seat, which can be manufactured separately. The heater and the gas-inlet aperture can be provided on the fixing seat. The sealing ring is provided between the sealing seat and the casing body, so as to fix them together. The fixing seat is supported by the sealing seat, hence the fixing seat can be made of a heat-resistant material such as ceramics, silicon rubber and the like, whilst the sealing seat can be made of normal metals or non-metallic materials, so as to give full scope to the heating-resistant characteristic of the fixing seat, and the connecting characteristic of the sealing seat, and to simplify the structure of the manufacturing mold itself. In addition, because the fixing seat contacts the heater directly, part of the heat from the heater can be stored by the fixing seat, which can be used to keep the air in the connection-passage and some liquid in the liquid-guiding device above the connection-passage under high temperature, which is good for atomizing the liquid drops in the connection-passage and also good for the permeation of the liquid in the liquid-guiding device to be atomized.

The liquid-container has a bottle-shaped body with a containing cavity, having a mouth part, from which the liquid in the liquid-container flows out. Liquid can be filled into the liquid-container before use or assembly. The liquid-container can be manufactured either integral with the casing body, or separately. The shape of the mouth part of the liquid-container can be either of the necked type or open type.

When the shape of the mouth part of the liquid-container is of the necked type, the liquid-guiding device can be inserted into the open end of the liquid-container directly, or when the liquid-container is dismountable, a spacer can be positioned in the open end of the liquid-container at first and then the liquid-guiding device is inserted into. Of course it is also a possibility for the total of or just part of the liquid-guiding device to be inserted into the mouth part of the liquid-container, anyway, the liquid in the liquid-container should permeate out slowly.

When the shape of the mouth part of the liquid-container is of the open type, a position step can be provided at the inside of the mouth part of the liquid-container. The mouth part of the liquid-container can be plugged in advance by the spacer provided on the position step. There are liquid-draining apertures on the spacer, and the liquid-guiding device is located under the spacer and closing the liquid-draining apertures, the co-operation of the spacer and the liquid-guiding device thus plug the mouth part of the liquid-container. The liquid in the liquid-container then permeates out to the liquid-guiding device through the liquid-draining apertures. In addition, the spacer can limit the assembled depth of the liquid-guiding device, so as to prevent the liquid-guiding device from being inserted too far into the liquid-container in assembly, or to prevent the liquid-guiding device moving too far towards the liquid-container when the rear closure is supported against the liquid-guiding device.

The mouth part of the liquid-container is plugged by the liquid-guiding device is to say that the liquid-guiding device is provided just at the inside of the mouth part of the liquid-container or just right at the opening of the mouth part of the liquid-container, from which the liquid-guiding device can either prevent the liquid draining directly out from the mouth part of the liquid-container, and also can absorb the liquid in the liquid-container. The liquid in the liquid-container which is going to be atomized then continuously enters into the liquid-guiding device by way of permeation. The liquid-guiding device is provided just at the inside of the mouth part of the liquid-container or just right at the opening of the mouth part of the liquid-container, and is not provided in the space of the liquid-container for storage liquid, that is also to say there is no medium in the liquid-container for storing liquid. In order to avoid an insufficient seal or a gap between the liquid-guiding device and the mouth part of the liquid-container, it is preferred to insert at least part of the liquid-guiding device directly into the inside of the mouth part of the liquid-container. The liquid-guiding device can be made of resilient materials, such as cellucotton or sponge or the like, having heat-resistant, non-toxic and multi-apertured characteristics.

In order to make the permeating of the liquid in the liquid-container easier, the further preferred embodiment is to arrange a gas pipe in the liquid-container, with one end of the gas pipe inserted in the liquid-guiding device, and another end of the gas pipe extending to the upper part of the liquid-container. The air from the outside of the liquid-container thus penetrates slowly into the liquid-container along the gas pipe so as to avoid an excessive negative pressure in the liquid-container. It is preferred that one end of the gas pipe does not penetrate through the liquid-guiding device, so as to achieve the semi-sealing for the gas pipe by making use of part of the wall of the liquid-guiding device, whilst the air permeates slowly into the gas pipe.

The connection-passage is the passage for airflow, which is provided between the liquid-guiding device and the rear closure. The air from outside passes through the atomizer, and then passes through the connection-passage, and then enters into the airflow-passage between the casing body and the liquid-container, thus the heated and atomized liquid flows along the airflow-passage.

There are many kinds of method of forming the connection-passage, one of them is to arrange a depressed cavity at the center of the top end of the rear closure (or the fixing seat), with the air-inlet port connected to the depressed cavity, the heater being arranged across the side-wall around the depressed cavity, through-apertures are provided on the side-wall of the depressed cavity. Hence, the side-wall around the upper end of the depressed cavity then supports the heater against the liquid-guiding device and also under the liquid-guiding device, the depressed cavity thus can be deemed as the connection-passage (as well as the atomizing cavity). The atomized liquid (gas) then passes through the through-apertures on the side-wall of the depressed cavity and enters into the airflow-passage between the casing body and the liquid-container. Another equivalent method of forming the connection-passage is to arrange convex columns on the upper end of the rear closure (or the fixing seat), the heater is located across the convex columns. The space surrounding the convex columns then forms the connection-passage (namely the atomizing cavity). Secondly, the method also can be of course a combination of the two methods mentioned above. The connection-passage thus can be naturally formed by the incorporation of the side-wall of the depressed cavity or the convex columns with the liquid-guiding device; once the rear closure (or the fixing seat) has been assembled to support against the liquid-guiding device, the problem, such as the connection-passage becoming deformed or blocked, can be thus avoided, and also it is ensured that the heater is located in the connection-passage and also against the liquid-guiding device.

The heater is a part used for heating and atomizing liquid which is positioned on the upper end of the rear closure, so as to contact the liquid-guiding device as much as possible, so that the heater can absorb the liquid on the liquid-guiding device. Secondly, because at least part of the heater is positioned in the connection-passage, the liquid-drops spreading in the connection-passage and on the heater can be atomized by using the heater and can be taken away by the flowing air out to the airflow-passage between the casing body and the liquid-container. The heater can comprises a wire wound around the heat-resisting fibre core, which can make the spreading of the liquid on the liquid-guiding device easier. Further, benefiting from that the heat-resisting fibre core connecting or being near to the liquid-guiding device, liquid drops spreading from the liquid-guiding device and the heater can be absorbed, more liquid drops can be then heated and atomized by the heater. Alternatively, a spreading spacer can be placed at the lower surface of the liquid-guiding device, with the heater contacting the lower surface of the spreading spacer, from which the liquid in the liquid-guiding device can be spread evenly by using the spreading spacer. The spreading spacer is a kind of flat material, with a better spreading characteristic, whilst not necessarily having a better liquid-storing characteristic than the liquid-guiding device. The spreading spacer can be stuck to the lower surface of the liquid-guiding device. The electrode leg wire of the heater extends through the rear closure and connects to an external power source.

At least part of the heater is located in the connection-passage across the upper end of the rear closure and also contacts the lower surface of the liquid-guiding device or the spreading spacer, and hence it is impossible for the external surface of the heater to be totally exposed in the connection-passage.

For the convenience of assembly and using the heater, it is preferred to arrange a semicircular-shaped groove, which should match the heater, on the upper end of the rear closure, the heater should be erected in the semicircular-shaped groove. Hence, under the abutment by the upper end of the rear closure, good contact can be achieved between the heater and the lower surface of the liquid-guiding device or the spreading spacer, whilst ensures that the heater located in the connection-passage.

According to the embodiments disclosed above, the liquid-container is filled with liquid medium which is going to be atomized, the liquid-container is located in the casing body, then the liquid-guiding device plugs the mouth part of the liquid-container, further, the rear closure provided with the heater is fixed at the opening of the rear end of the casing body, with the upper end of the rear closure (or the fixing seat) abutting against the lower surface of the liquid-guiding device, so that the connection-passage to be formed between the upper end of the rear closure (or the fixing seat) and the liquid-guiding device. Thus, the liquid in the liquid-container spreads to the connection-passage by the liquid-guiding device or the spreading spacer placed at the lower surface of the liquid-guiding device. The flowing air will take the atomized gas out when the heater heats.

The embodiments described above is simple in structure and easy to assemble with a good sealing effect, in addition, there are still the following main beneficial effects:

1) because the heater is located on the upper end of the rear closure, and contacts the lower surface of the liquid-guiding device or the spreading spacer provided under the liquid-guiding device, it is easy for the heater itself or the fibre core of the heater to absorb liquid just by using of the wicking ability and gravity action of the liquid itself.

2) because no medium provided in the liquid-container for storing liquid, the quantity of the liquid able to be stored in every atomizer of the electronic atomizing inhaler is substantially increased for the same volume of liquid-container, which leads to a durable use and also have resolved the defects of the traditional products, in which a medium has to be used for storing liquid.

3) because the liquid-container is plugged at its mouth part by the liquid-guiding device, the sealing and the draining out for the liquid in the liquid-container can be achieved by making use of the principle of negative pressure and the adhesive characteristic of the liquid itself.

4) because the convex columns are provided on the upper end of the rear closure (or the fixing seat) and the heater is erected on the convex columns, the connection-passage thus is formed in the space around the convex columns, when the rear closure (or the fixing seat) has been assembled to abut against the liquid-guiding device, the problem of the connection-passage becoming deformed or blocked up can be avoided, and also ensures that the heater is located in the connection-passage.

Because of such advantages and characteristics mentioned above, the present invention can be applied to the product of an electronic atomizing inhalator.

BRIEF DESCRIPTION OF THE DRAWINGS

Embodiments of the atomizer of the electronic atomizing inhalator of the present invention will now be described with reference to the accompanying drawings, in which.

DETAILED DESCRIPTION OF THE EMBODIMENTS

Figure 1:
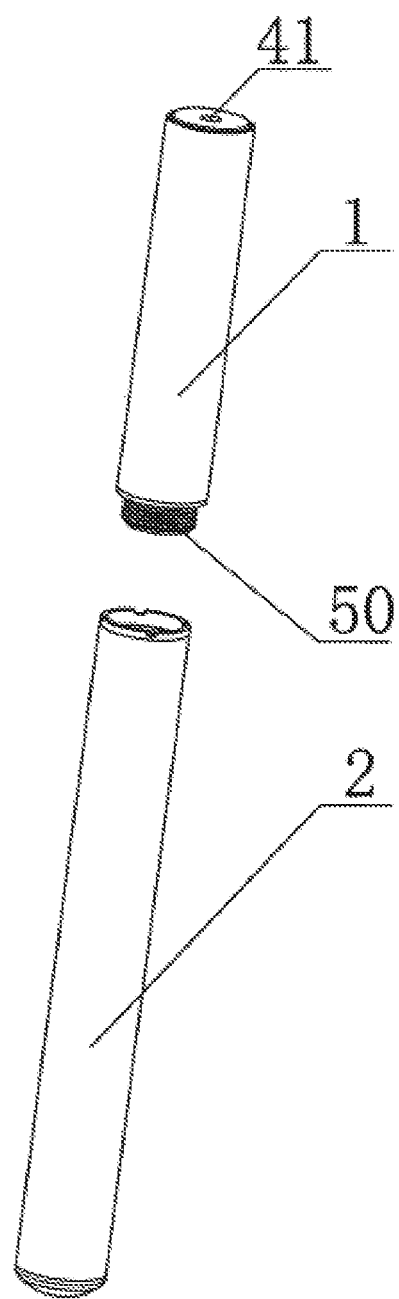
FIG. 1 is a schematic illustration of the assembly of the atomizer of an electronic atomizing inhaler of the present invention with the power supply.

As shown in FIG. 1 of the drawings, the electronic atomizing inhaler is a kind of product for atomizing a liquid contained therein, so as to allow the consumer to inhale the atomized gas or fogged liquid therefrom. The inhaler comprises a cylindrical atomizer 1 and a cylindrical control and power portion 2, which are electrically and mechanically connected to each other by a screw-threaded electrode 50. The control and power portion 2 includes a power supply and a control circuit etc. The control and power portion 2 is arranged to apply electric power to the atomizer 1 and is detachably connected to the atomizer 1 by the screw-threaded electrode 50.

Figure 2:
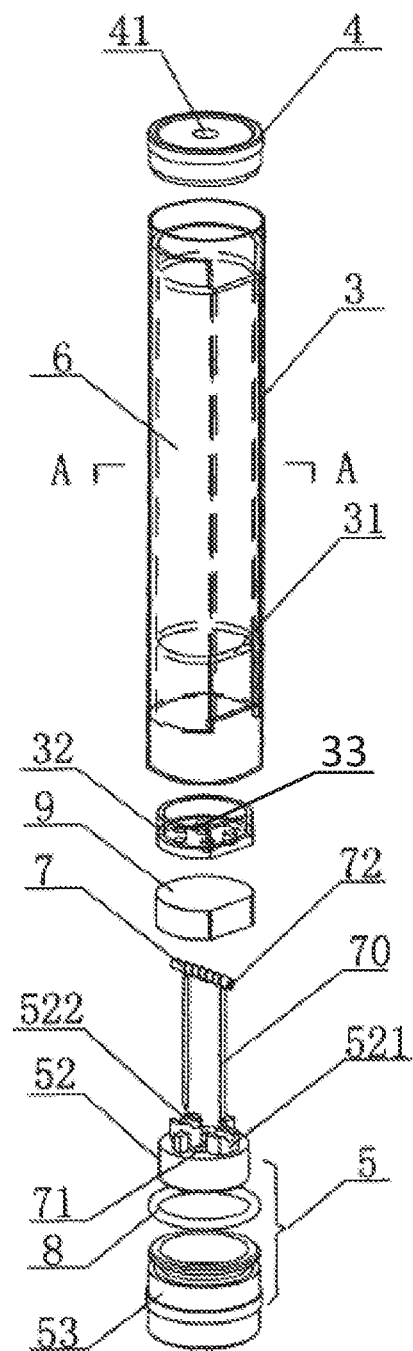
FIG. 2 is an exploded schematic illustration of the atomizer of the electronic atomizing inhalator of the present invention.
Figure 3:
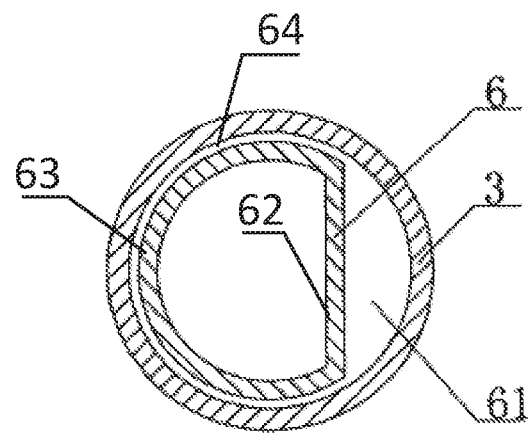
FIG. 3 is a sectional view along the line A-A of FIG. 2.
Figure 4:
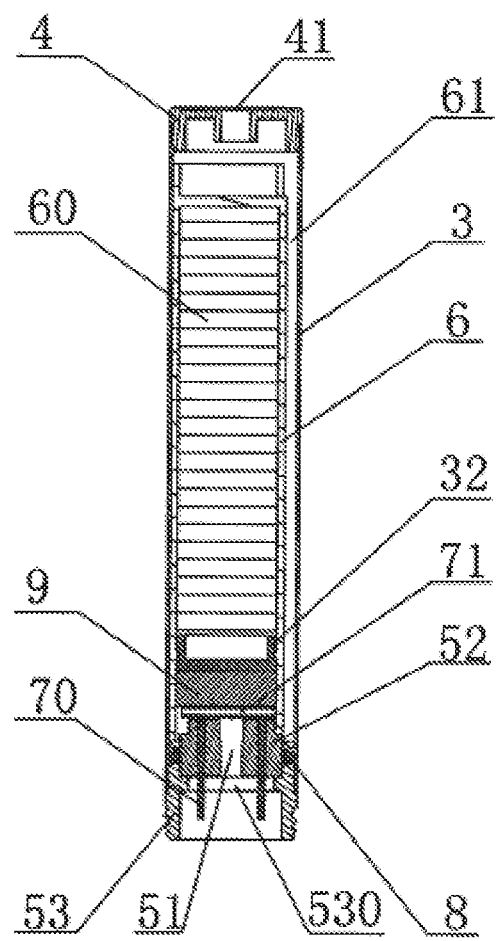
FIG. 4 is a sectional schematic illustration of the atomizer of the electronic atomizing inhalator of the present invention.

As shown in FIGS. 2 to 4 of the drawings, the atomizer 1 of the electronic atomizing inhaler comprises a tubular casing body 3.

A closure wall 4 is provided at the opening of the front end of the casing body 3. A gas-outlet aperture 41 is defined on the closure wall 4. The closure wall 4, like a cap, engagingly receives in the opening at the front end of the casing body 3. The gas-outlet aperture 41 conveniently permits the outflow of atomized gas, so that the consumer can inhale the atomized gas in the atomizer 1 through the gas-outlet aperture 41.

A rear closure 5 is provided at the opening of the rear end of the casing body 3. A gas-inlet aperture 51 is defined in the rear closure 5. It is noted that the front end of the casing body 3 is designated as the near end near the mouth of the consumer when the atomizer 1 being used. The rear end of the casing body 3 is designated as the far end far from the mouth of the consumer, compared with the near end, when the atomizer 1 being used. The rear closure 5 comprises a fixing seat 52 and a hollow tubular sealing seat 53 engaged with the fixing seat 52, the gas-inlet aperture 51 being provided on the fixing seat 52. A bigger central aperture 530 is provided in the horizontal board part of the sealing seat 53. The central aperture 530 is communicated with the gas-inlet aperture 51, and can be configured as a part of the gas-inlet passage for air flowing into the casing body 3.

Two convex columns 521 are provided on the upper end of the fixing seat 52, with semicircular-shaped grooves 522 being provided on the upper end of the convex columns 521. A heater 7 is mounted on the two convex columns 521. The heater 7 comprises a heat-resistant fibre core 72 and a wire (not labeled) combined with the fibre core 72. The fibre core 72 is at least partly received in the grooves 522. Two electrode leg wires 70 extend from the two ends of the wire of the heater 7, insert through the fixing seat 52 and then electrically connect to the control and power portion 2 by the screw-threaded electrode 50. Screw thread is provided on the outside of the lower end of the sealing seat 53, functioning as one pole of the screw-threaded electrode 50. Another pole of the screw-threaded electrode 50 is not shown in the Figures. The hollow tubular sealing seat 53 is fixed in the opening at the rear end of the casing body 3 with a sealing ring 8 sandwiched between the outside of the sealing seat 53 and the inner wall of the casing body 3. A step (not labeled) is provided in the cavity of the sealing seat 53. The central aperture 530 is defined at the center of the step. The fixing seat 52 is fixed in the upper part of the cavity of the sealing seat 53 and arranged on the step. The fixing seat 52 is elastic to provide a good sealing effect between the fixing seat 52 and the sealing seat 53, and also provide a certain elasticity when the fixing seat 52 abuts against the lower surface of the liquid-guiding device 9, so as to make the heater 7 more adjacent to the lower surface of the liquid-guiding device 9. The fixing seat 52 can be made from a heat-resisting silicon rubber.

As shown in FIGS. 2 to 4 of the drawings, there is also a liquid-container 6 provided in the cavity formed by the casing body 3, closure wall 4 and rear closure 5. The heater 7 and the liquid-guiding device 9 are arranged between the rear closure 5 and the liquid-container 6.

The liquid-container 6 comprises a bottle-shaped body having a container cavity. The liquid-container 6 has a wide mouth part facing towards the liquid-guiding device 9, the inside diameter of the mouth part being at least equal to the inside diameter of the cavity of the liquid-container 6. No medium for storing liquid is provided in the liquid-container 6. The liquid 60 to be atomized can be introduced into the liquid-container 6 before the inhaler is used or assembled. The liquid-container 6 and the casing body 3 can be manufactured separately, so as to lower the difficulty of making molds.

The liquid-guiding device 9 is a kind of part for preventing the liquid 60 draining directly out from the mouth part of the liquid-container 6. Particularly, the liquid-guiding device 9 can absorb the liquid 60 stored in the liquid-container 6 by way of continuous permeation.

Figure 5:
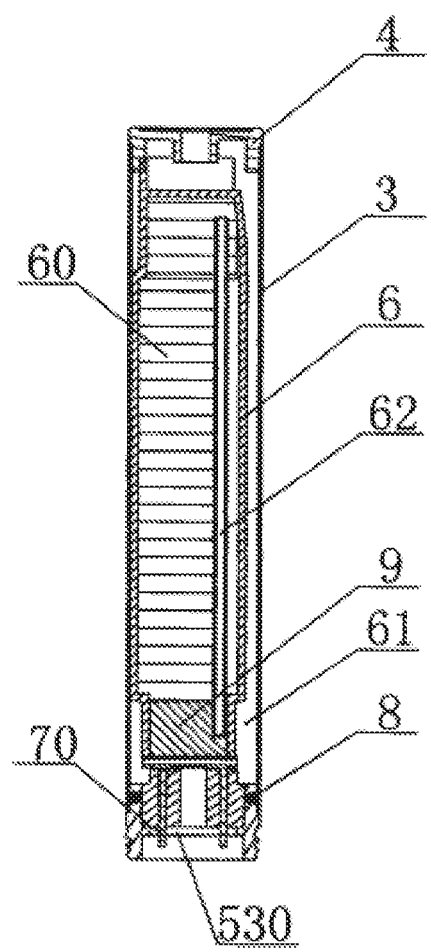
FIG. 5 is a schematic illustration having a gas pipe on the base of the embodiment shown in FIG. 2 and FIG. 4, whilst the shape of the mouth part of the liquid-container is of the necked type.

As shown in FIG. 5, in order to make the liquid 60 in the liquid-container 6 permeate more easily, a gas pipe 62 is arranged in the liquid-container 6 in an alternative embodiment, with one end of the gas pipe 62 inserting in the liquid-guiding device 9, while not penetrating through the wall of the liquid-guiding device 9, and another end of the gas pipe 62 extending to the upper part of the liquid-container 6, which allows the air from the outside of the liquid-container 6 to flow slowly into the liquid-container 6 along the gas pipe 62, so as to avoid an excessive negative pressure in the liquid-container 6. The liquid-guiding device 9 can be made from cellucotton or sponge, which should be a heat-resisting, non-toxic and porous material.

As shown in FIG. 2 and FIG. 4, a position-step 31 is provided at the inside of the mouth part of the liquid-container 6. The liquid-container 6 can be plugged by a cap-shaped spacer 32 placed on the position step 31, with liquid-draining apertures 33 provided on the spacer 32. The spacer 32 thus plugs the mouth part of the liquid-container 6 in advance. The liquid-guiding device 9 is inserted into the mouth part of the liquid-container 6 and abuts the spacer 32, thus slowly guides the liquid 60 in the liquid-container 6 out to the liquid-guiding device 9. In addition, the spacer 32 also limits the assembled depth of the liquid-guiding device 9, so as to avoid the liquid-guiding device 9 being inserted too far into the liquid-container 6 during assembly, and also to prevent the liquid-guiding device 9 from moving towards the liquid-container 6 when the rear closure 5 abuts against the liquid-guiding device 9. The spacer 32 is cap-shaped, which makes it easy for the spacer 32 to be positioned at the inside of the mouth part of the liquid-container 6.

As shown in FIG. 5, the shape of the mouth part of the liquid-container 6 can be of a necked type in an alternative embodiment. The liquid-guiding device 9 then is directly inserted into the mouth part of the liquid-container 6.

As shown in FIG. 3 and FIG. 4, an airflow-passage 61 is provided between the casing body 3 and the liquid-container 6 to communicate with the gas-outlet aperture 41 and the gas-inlet aperture 51, which can be either arranged to be around the liquid-container 60 or at just one or two side(s) of the liquid-container 6. In this embodiment, a part 62 of the sidewall of the liquid-container 6 is flat, and other part 63 of the sidewall of the liquid-container 6 is curved. The flat-shaped sidewall 62 forms a circumferential part of the sidewall of the liquid-container 6, and the curved sidewall 63 forms the remainder circumferential part of the sidewall of the liquid-container 6. The flat-shaped sidewall 62 has an elongated extending direction along the axial direction of the liquid-container 6. The curved sidewall 63 also has an elongated extending direction along the axial direction of the liquid-container 6. The airflow-passage 61 is formed between the flat-shaped sidewall 62 of the liquid-container 6 and the casing body 3. A gap 64 is defined between the curved sidewall 63 and the casing body 3. The dimension of the gap 64 is dramatically smaller than that of the airflow-passage 61. Also referring to FIG. 5, the closure wall 4 provided at the front end of the casing body 3 blocks or rests on the top end of the curved sidewall 63, such that the closure wall 4 closes the gap 64 and hence the gas-outlet aperture 41 directly communicates with the airflow-passage 61, but not directly communicates with the gap 64. The gas-outlet aperture 41 indirectly communicating with the gap 64 means the gas-outlet aperture 41 communicating with the gap 64 via the airflow-passage 61.

As shown in FIG. 2 and FIG. 4, because of the two convex columns 521 are provided on the upper end of the fixing seat 52, the space between the two convex columns 521 and the space around thereof thus form a connection-passage 71 for air-flowing passing through. The air outside enters into the atomizer 1 from the gas-inlet aperture 51, passes through the connection-passage 71, and then enters into the airflow-passage 61, the heated and atomized liquid then flows out along the airflow-passage 61 and the gas-outlet aperture 41.

Another embodiment that can be implemented (not shown in Figures) is to define a depressed cavity at the center of the upper end of the fixing seat 52, which is connected to the gas-inlet aperture 51, the fibre core 72 is radially-arranged across the top end of the side-wall around the depressed cavity, with through-apertures provided on the side-wall of the depressed cavity, hence, the side-wall around the upper end of the fixing seat 52 supports the heater 7 against the liquid-guiding device 9 and the heater 7 is also under the liquid-guiding device 9. In such instance, the depressed cavity then acts as the connection passage 71 (as well as the atomizing cavity), the atomized liquid (gas, or fogged liquid) then passes through the through-apertures on the side-wall of the depressed cavity and enters into the airflow-passage 61 between the casing body 3 and the liquid-container 6.

As shown in FIG. 2 and FIG. 4, the heater 7 is a kind of part used for heating and atomizing liquid, which is positioned on the tops of the convex columns 521 of the fixing seat 52 and is also located in the groove 522, for the convenience of the heater 7 contacting the liquid-guiding device 9 as much as possible. Because the heater 7 itself absorbs the liquid on the liquid-guiding device 9, the liquid-drops spreading in the connection-passage 71 and on the heater 7 can be atomized by the heater 7 and can be carried away by the flowing air to the airflow-passage 61. The wire of the heater 7 can be wound around the heat-resistant fibre core 72 to make it easier for the heat-resistant fibre core 72 to absorb the liquid transferred from the liquid-guiding device 9 and the heater 7, and for the heater 7 to atomize the liquid-drops as much as possible.

Another embodiment (not shown in the Figures) is to arrange a spreading-spacer at the lower surface of the liquid-guiding device 9. The heater 7 contacts the lower surface of the spreading-spacer, from which the liquid on the liquid-guiding device 9 can be spread more evenly by using the spreading-spacer. The spreading-spacer is a kind of flat-shaped material, with improved spreading characteristics compared with the liquid-guiding device 9, whilst not necessary better liquid-storage characteristics than the liquid-guiding device 9. The spreading-spacer can be adhered to the lower surface of the liquid-guiding device 9.

According to the embodiments described above, the liquid-container 6 can be positioned in the casing body 3, with liquid 60 filled in the liquid-container 6, then the liquid-container 6 is plugged at its mouth part by the liquid-guiding device 9 and the spacer 32. The rear closure 5, provided with the heater 7, can be assembled into the opening of the rear end of the casing body 3, with the upper end of the rear closure 5 and the heater 7 abutting against the liquid-guiding device 9. The connection-passage 71 is provided between the upper end of the rear closure 5 and the liquid-guiding device 9. Hence, the liquid 60 in the liquid-container 6 permeates into the connection-passage 71, the heater 7 and the heat-resisting fibre core 72 by the liquid-guiding device 9 or the spreading-spacer provided at the lower surface of the liquid-guiding device 9. When the heater 7 is operated, the liquid 60 is atomized and the atomized gas will be drawn out together with the airflow.

What is claimed is:

1. An atomizer of an electronic atomizing inhaler, comprising:
   a liquid-container with liquid contained therein, the liquid-container having a mouth part;
   a spacer provided at the mouth part of the liquid-container, wherein a plurality of liquid-draining apertures are formed on the spacer;
   a liquid-guiding device attached to a bottom surface of the spacer, the liquid-guiding device closing the mouth part of the liquid-container and blocking the liquid-draining apertures of the spacer, wherein the liquid-guiding device is configured to prevent the liquid from draining directly out of the mouth part of the liquid-container; and
   a heater atomizing the liquid that penetrates through the liquid-guiding device;
   wherein a position-step is formed at an inside of the mouth part, and the spacer is placed on the position-step.

2. The atomizer of claim 1, wherein the spacer is cap-shaped and has the bottom surface and a side surface extending upwardly from an edge of the bottom surface.

3. The atomizer of claim 1, wherein the liquid-guiding device comprising a top surface facing towards the spacer and a bottom surface facing away from the spacer, both of the top surface and the bottom surface of the liquid-guiding device are flat.

4. The atomizer of claim 1, wherein the liquid-guiding device comprising a top surface facing towards the spacer and a bottom surface facing away from the spacer, the shape of the top surface of the liquid-guiding device and the shape of the bottom surface of the liquid-guiding device are same to the shape of the bottom surface of the spacer.

5. The atomizer of claim 1, wherein a cross-section of the liquid-container perpendicular to a longitudinal direction of the liquid-container has the same shape as the shape of the bottom surface of the spacer.

6. The atomizer of claim 1, wherein the mouth part of the liquid-container has an inside diameter being at least equal to an inside diameter of a cavity of the liquid-container, a position-step is formed at the inside of the mouth part, and the spacer is provided between the position-step and the liquid-guiding device.

7. The atomizer of claim 1, further comprising a spreading-spacer provided between a lower surface of the liquid-guiding device and the heater.

8. The atomizer of claim 1, wherein a gas pipe is arranged in the liquid-container, with one end of the gas pipe extending into the liquid-guiding device, and another end of the gas pipe extending to an upper part of the liquid-container.

9. The atomizer of claim 1, further comprising:
   a tubular casing body with a cavity formed therein and two openings at front and rear ends thereof communicated with the cavity, the cavity and the two openings communicating with each other to form an airflow-passage; and
   a cap provided at the opening of the front end of the casing body, a gas-outlet aperture being defined in the cap and communicated with the airflow-passage;
   wherein the liquid-container is provided in the cavity of the casing body, and the mouth part of the liquid-container is opposing to the cap.

10. The atomizer of claim 9, wherein the liquid-container comprises a curved sidewall forming a circumferential part of the sidewall of the liquid-container and a flat sidewall forming a remainder circumferential part of the sidewall of the liquid-container, the airflow-passage is formed between the flat sidewall and the casing body, a gap is defined between the curved sidewall and the casing body, the cap rests on the curved sidewall to close the gap and hence the gas-outlet aperture directly communicates with the airflow-passage, and indirectly communicates with the gap via the airflow-passage.

11. The atomizer of claim 1, wherein the liquid-container has no liquid storage medium contained therein.

12. The atomizer of claim 1, wherein the heater is capable of absorbing the liquid in the liquid-guiding device.

13. An electronic atomizing inhaler, comprising an atomizer and a control and power portion electrically and mechanically connected to the atomizer; the atomizer comprising:
   a liquid-container with liquid contained therein, the liquid-container having a mouth part;
   a spacer provided at the mouth part of the liquid-container, wherein a plurality of liquid-draining apertures are formed on the spacer;
   a liquid-guiding device attached to a bottom surface of the spacer, the liquid-guiding device closing the mouth part of the liquid-container and blocking the liquid-draining apertures of the spacer, wherein the liquid-guiding device is configured to prevent the liquid from draining directly out of the mouth part of the liquid-container; and
   a heater atomizing the liquid that penetrates through the liquid-guiding device;
   wherein a position-step is formed at an inside of the mouth part, and the spacer is placed on the position-step.

14. The electronic atomizing inhaler of claim 13, wherein the spacer is cap-shaped and has the bottom surface and a side surface extending upwardly from an edge of the bottom surface.

15. The electronic atomizing inhaler of claim 13, wherein the atomizer further comprises a cap provided at an opening of a front end of a casing body, a gas-outlet aperture being defined in the cap and communicated with an airflow-passage; the liquid-container comprises a curved sidewall and a flat sidewall, the airflow-passage is formed between the flat sidewall and the casing body, a gap is defined between the curved sidewall and the casing body and is closed by the cap at the front end of the casing body, and the gas-outlet aperture directly communicates with the airflow-passage, and indirectly communicates with the gap via the airflow-passage.

16. The electronic atomizing inhaler of claim 13, wherein the liquid-guiding device comprising a top surface facing towards the spacer and a bottom surface facing away from the spacer, both of the top surface and the bottom surface of the liquid-guiding device are flat.

17. The electronic atomizing inhaler of claim 13, wherein the liquid-guiding device comprising a top surface facing towards the spacer and a bottom surface facing away from the spacer, the shape of the top surface of the liquid-guiding device and the shape of the bottom surface of the liquid-guiding device are same to the shape of the bottom surface of the spacer.

18. The electronic atomizing inhaler of claim 13, wherein a cross-section of the liquid-container perpendicular to a longitudinal direction of the liquid-container has the same shape as the shape of the bottom surface of the spacer.

\* \* \* \* \*